US007491677B2

(12) United States Patent
Castellano et al.

(10) Patent No.: US 7,491,677 B2
(45) Date of Patent: Feb. 17, 2009

(54) COMBINATORIAL SYNTHESIS

(75) Inventors: Christopher R. Castellano, Ringoes, NJ (US); Ahmad Moini, Princeton, NJ (US); Gerald S. Koermer, Roseland, NJ (US)

(73) Assignee: BASF Catalysts LLC, Florham Park, NJ (US)

( * ) Notice: Subject to any disclaimer, the term of this patent is extended or adjusted under 35 U.S.C. 154(b) by 849 days.

(21) Appl. No.: 10/611,385

(22) Filed: Jul. 1, 2003

(65) Prior Publication Data

US 2004/0028815 A1  Feb. 12, 2004

(51) Int. Cl.
*B01J 21/04* (2006.01)
(52) U.S. Cl. .................................. 502/439; 502/527.23
(58) Field of Classification Search ................. 502/439, 502/527.23
See application file for complete search history.

(56) References Cited

U.S. PATENT DOCUMENTS

| | | | |
|---|---|---|---|
| 5,959,297 A | 9/1999 | Weinberg et al. | 250/288 |
| 5,985,356 A | 11/1999 | Schultz et al. | 427/8 |
| 6,004,617 A | 12/1999 | Schultz et al. | 427/8 |
| 6,030,917 A | 2/2000 | Weinberg et al. | 502/104 |
| 6,034,775 A | 3/2000 | McFarland et al. | 356/364 |
| 6,045,671 A | 4/2000 | Wu et al. | 204/298.11 |
| 6,182,499 B1 | 2/2001 | McFarland et al. | 73/24.06 |
| 6,187,164 B1 | 2/2001 | Warren et al. | 205/81 |
| 6,248,540 B1 | 6/2001 | Weinberg et al. | 435/7.1 |
| 6,326,090 B1 | 12/2001 | Schultz et al. | 428/688 |
| 6,346,290 B1 | 2/2002 | Schultz et al. | 427/8 |
| 6,364,956 B1 | 4/2002 | Wang et al. | 118/726 |
| 6,514,764 B1 | 2/2003 | Willson | |
| 2003/0073246 A1 | 4/2003 | Ting et al. | 436/180 |

FOREIGN PATENT DOCUMENTS

| | | |
|---|---|---|
| EP | 1129773 | 9/2001 |
| WO | WO 98/14641 | 4/1998 |
| WO | WO 98/15969 | 4/1998 |
| WO | WO 98/47613 | 10/1998 |
| WO | WO 99/19724 | 4/1999 |
| WO | WO 00/17413 | 3/2000 |
| WO | WO 00/29844 | 5/2000 |
| WO | WO 00/43119 | 7/2000 |
| WO | WO 02/24321 A1 | 3/2002 |

OTHER PUBLICATIONS

Hanak, J.J. "The 'Multiple-Sample Concept' in Materials Research: Synthesis, Compositional Analysis and Testing of Entire Multicomponent Systems." 1970. Journal of Materials Science, pp. 964-971.
G.C. Moreland, R. Johnson. "Preparation of Multiple Microprobe Samples." 1975. Smithsonian Contributions to Earth Sciences, pp. 87-88.
I. Goldfarb, E. Zolotoyabko, A. Berner, D. Shechtman. "Novel Sample Preparation Technique for the Study of Multicomponent Phase Diagrams." Materials Letters 21 (1994), pp. 149-154.
K. Govindaraju and G. Mevelle. "Fully Automated Dissolution and Separation Methods for Inductively Coupled Plasma Atomic Emission Spectrometry Rock Analysis." Journal of Analytical Atomic Spectrometry, Sep. 1987, vol. 2, pp. 615-621.
R.B. van Dover, L.F. Schneemeyer, R. M. Fleming. "Discovery of a Useful Thin-Film Dielectric Using a Composition-Spread Approach." Nature, vol. 392, Mar. 1998, pp. 162-164.

*Primary Examiner*—Edward M Johnson
(74) *Attorney, Agent, or Firm*—Raymond F. Keller; Greg Turocy

(57) ABSTRACT

Methods are disclosed for providing a library of composite or novel composition samples on a support. The method involves depositing one or more components as concentration gradients on the surface of the support. The concentration gradients are placed on the support in the form of superimposed triangles which allow ready formation of composite or composition samples containing three or more components. The samples can be removed from the support by drilling out portions of the coated support so as to yield individual tablets containing the support with one or more component layers thereon. By using this method, a vast number of samples can be made.

40 Claims, 6 Drawing Sheets

COMBINATORIAL SYNTHESIS

FIELD OF THE INVENTION

This invention is directed to a method for preparation of large numbers of sample materials suitable for combinatorial screening. Depositing individual components as concentration gradients thereof onto a substrate forms the samples. A novel shaped coating gradient allows a plurality of coatings to be formed as continuous concentration gradients along a substrate surface and for readily generating libraries of all possible combinations of components. The gradient shape readily allows for accurately determining the composition of each sample on the substrate surface. Samples attached to the substrate and from different regions of the gradient can be screened for any number of useful properties including, but not limited to, physical, electrical, and chemical properties and any numerous subsets of such properties.

BACKGROUND OF THE INVENTION

Combinatorial Chemistry, also known as High Throughput Experimentation, is an emerging area that has impacted various fields. Although still evolving, the procedure is fully established in the pharmaceutical industry. There is increasing interest in applying such techniques in materials science since the combinatorial synthesis method can be a very powerful tool in increasing the rate of experimentation, and therefore, improving the possibility for making discoveries.

The discovery of new materials with novel chemical and physical properties often leads to the development of new and useful technologies. Over forty years ago, for example, the preparation of single crystal semiconductors transformed the electronics industry. Currently, there is a tremendous amount of activity being carried out in the areas of superconductivity, magnetic materials, phosphors, nonlinear optics and high strength materials. Unfortunately, even though the chemistry of extended solids has been extensively explored, few general principles have emerged that allow one to predict with certainty composition, structure and reaction pathways for the synthesis of such solid state compounds. Importantly, it is difficult to predict a priori the physical and chemical properties a particular composition and structure will possess.

Clearly, the preparation of new materials with novel or desired chemical and physical properties is at best happenstance with our current level of understanding. Consequently, the discovery of new materials is limited by the ability to synthesize and analyze new compounds or compositions. As such, there exists a need in the art for a more efficient, economical and systematic approach for the synthesis of novel materials and for the screening of such materials for useful properties.

One of the processes whereby nature produces molecules having novel functions involves the generation of large collections (libraries) of molecules and the systematic screening of those libraries for molecules having a desired property. An example of such a process is the humoral immune system which in a matter of weeks sorts through some $10^{12}$ antibody molecules to find one which specifically binds a foreign pathogen (Nisonoff, et al., *The Antibody Molecule* (Academic Press, New York, 1975)). This notion of generating and screening large libraries of molecules has recently been applied to the drug discovery process. The discovery of new drugs can be likened to the process of finding a key which fits a lock of unknown structure. One solution to the problem is to simply produce and test a large number of different keys in the hope that one will fit the lock.

Using this logic, methods have been developed for the synthesis and screening of large libraries up to $10^{14}$ molecules) of peptides, oligonucleotides and other small molecules. Geysen, et al., for example, have developed a method wherein peptide syntheses are carried out in parallel on several rods or pins (see, J. Immun. Meth. 102:259-274 (1987), incorporated herein by reference). Generally, the Geysen, et al. method involves functionalizing the termini of polymeric rods and sequentially immersing the termini in solutions of individual amino acids. In addition to the Geysen, et al. method, techniques have recently been introduced for synthesizing large arrays of different peptides and other polymers on solid surfaces. Pirrung, et al. have developed a technique for generating arrays of peptides and other molecules using, for example, light-directed, spatially-addressable synthesis techniques (see, U.S. Pat. No. 5,143,854 and PCT Publication No. WO 90/15070, incorporated herein by reference. In addition, Fodor, et al. have developed, among other things, a method of gathering fluorescence intensity data, various photosensitive protecting groups, masking techniques, and automated techniques for performing light-directed, spatially-addressable synthesis techniques (see, Fodor, et al., PCT Publication No. WO 92/10092, the teachings of which are incorporated herein by reference).

Using these various methods, arrays containing thousands or millions of different elements can be formed (see, U.S. Pat. No. 5,424,186, the teachings of which are incorporated herein by reference). As a result of their relationship to semiconductor fabrication techniques, these methods have come to be referred to as "Very Large Scale Immobilized Polymer Synthesis," or "VLSIPS™ technology. Such techniques have met with substantial success in, for example, screening various ligands such as peptides and oligonucleotides to determine their relative binding affinity to a receptor such as an antibody.

U.S. Pat. No. 5,985,356, issued Nov. 16, 1999, the entire content of which is herein incorporated by reference, discloses the combinatorial synthesis for making and testing an array of novel materials. This patent provides methods and apparatus for the preparation and use of a substrate having an array of diverse materials in predefined regions thereon. A substrate having an array of diverse materials thereon is prepared by delivering components of materials to predefined regions on the substrate, and simultaneously reacting the components to form at least two materials. Materials which can be prepared using the methods and apparatus of the present invention include, for example, covalent network solids, ionic solids and molecular solids. More particularly, materials which can be prepared include inorganic materials, intermetallic materials, metal alloys, ceramic materials, organic materials, organometallic materials, non-biological organic polymers, composite materials (e.g., inorganic composites, organic composites, or combinations thereof), etc. Once prepared, these reaction products can be screened in parallel or sequentially for useful properties including, for example, electrical, thermal, mechanical, morphological, optical, magnetic, chemical and other properties. As such, the patented invention provides methods and apparatus for the parallel synthesis and analysis of novel materials having new and useful properties.

In one embodiment of U.S. Pat. No. 5,985,356, a first component of a first material is delivered to a first region on a substrate, and a first component of a second material is delivered to a second region on the same substrate. Thereafter, a second component of the first material is delivered to the first region on the substrate, and a second component of the second material is delivered to the second region on the substrate. The process is optionally repeated, with additional components, to form a vast array of components at predefined, i.e., known, locations on the substrate. Thereafter, the components are simultaneously reacted to form at least two materials. The components can be sequentially or simultaneously delivered to predefined regions on the substrate in any stoichiometry, including a gradient of stoichiometries, using any of a number of different delivery techniques.

In another embodiment, a method is provided for forming at least two different arrays of materials by delivering substantially the same reaction components at substantially identical concentrations to reaction regions on both first and second substrates and, thereafter, subjecting the components on the first substrate to a first set of reaction conditions and the components on the second substrate to a second set of reaction conditions. Using this method, the effects of the various reaction parameters can be studied on many materials simultaneously and, in turn, such reaction parameters can be optimized. Reaction parameters which can be varied include, for example, reactant amounts, reactant solvents, reaction temperatures, reaction times, the pressures at which the reactions are carried out, the atmospheres in which the reactions are conducted, the rates at which the reactions are quenched, the order in which the reactants are deposited, etc.

In the delivery systems of the patented invention, a small, precisely metered amount of each reactant component is delivered into each reaction region. This may be accomplished using a variety of delivery techniques, either alone or in combination with a variety of masking techniques. For example, thin-film deposition in combination with physical masking or photolithographic techniques can be used to deliver various reactants to selected regions on the substrate. Reactants can be delivered as amorphous films, epitaxial films, or lattice and superlattice structures. Moreover, using such techniques, reactants can be delivered to each site in a uniform distribution., or in a gradient of stoichiometries. Alternatively, the various reactant components can be deposited into the reaction regions of interest from a dispenser in the form of droplets or powder. Suitable dispensers include, for example, micropipettes, mechanisms adapted from ink-jet printing technology, or electrophoretic pumps.

Once the components of interest have been delivered to predefined regions on the substrate, they are reacted using a number of different synthetic routes to form an array of materials. The components can be reacted using, for example, solution based synthesis techniques, photochemical techniques, polymerization techniques, template directed synthesis techniques, epitaxial growth techniques, by the sol-gel process, by thermal, infrared or microwave heating, by calcination, sintering or annealing, by hydrothermal methods, by flux methods, by crystallization through vaporization of solvent, etc. Thereafter, the array can be screened for materials having useful properties.

Similar to the formation of a large array of compositions as described in U.S. Pat. No. 5,985,356, is a technique for forming an array of different compositions, including metal alloys wherein the individual components that form the composition are applied by thin film deposition as continuous concentration gradients across a sheet. J. J. Hanak, "The 'Multiple-Sample Concept' in Materials Research: Synthesis, Compositional Analysis and Testing of Entire Multicomponent Systems", *Journal of Materials Science* 5 (1970) 964-971 discusses the development of multicomponent synthesis including the use of a technique of co-evaporating or co-sputtering two or more elements from different, physically separated sources onto a suitable substrate. In one experiment, almost the entire composition continuum of a given binary or ternary system was deposited on one substrate. Specimens made by the foregoing techniques have to be analyzed for chemical content point by point by existing chemical or physical methods. Thus the advantage gained by the synthesis technique was all but lost in the analytical methods. The article discloses that a unique computerized analytical method was developed based on the measurement of a simple extensive property common to all deposited films, namely, the thickness. In order to obtain analysis for the entire composition range the only required measurements are the two thickness measurements for a given binary system or three such measurements for a ternary system. The development of the computerized analysis is stated to have meant the removal of the main obstacle to the realization of the multiple sample concept. Goldfarb, et al., "Novel Sample Preparation Technique for the Study of Multiple Component Phase Diagrams", *Materials Letters* 21 (1994) 149-154, provides a technique for alloy sample preparation based on thin film deposition, for a study of binary and ternary compositions. Thin elemental wedge-shaped layers of the components were gradually sputtered in an alternating manner to form a multilayered structure. The samples obtained had compositions which depended upon the location of the substrate. Such samples, containing differently composed Au—Ag—Cu alloys were heat treated to promote formation of stable phases. The alloys formed were studied by x-ray diffraction and various microscopic techniques. The article demonstrates the advantages of the disclosed method over conventional bulk-based methods. A similar approach was taken to evaluate alternative thin-film dielectrics as described in *Letters to Nature*, "Discovery of a Useful Thin-film Dielectric Using a Composition-Spread Approach", R. B. van Dover, et al., *Nature* (vol. 392) Mar. 12, 1998. In this article, a wide range of compositions were efficiently evaluated by using a technique of depositing a single film with a ternary composition spread on a sheet and evaluating the critical properties as a function of position on the sheet which is directly related to material composition using an automated tool, the continuous composition spread technique.

Different from new materials in which new chemical compounds are formed from reaction mixtures of distinct reaction elements or compounds, or alloys, which are solid solutions of two or more components, are composite materials, which typically comprise one, or more components arranged as unreacted mixtures or layers. Composite materials are widely used for industrial and consumer use and are formed based upon the idea that a mixture of components can yield a better property configuration than a single base component. Among the numerous objects which can be formed as composites, non-limiting samples include heterogeneous catalysts, adsorbents for gas or liquid separations and pigments. Heterogeneous catalysts, for example, are widely used for industrial processing and/or in consumer goods, such as, for example, as oxidation catalysts contained in catalytic converters of automobiles. As opposed to new compounds from deposited reactive layers, the chemical compositions which form the distinct deposited compounds of heterogeneous catalysts remain mostly distinct from the other compounds. The activity of particular catalysts, the selectivity to achieve the desired product, thermal, hydro and hydrothermal stabilities of the heterogeneous catalysts often depend upon the distinct layered configuration of the deposited metal, metal oxide or other compounds as well as the distinct composition of each layer and/or thickness of each layer which are deposited to form the heterogeneous catalytic material. Moreover, often the heterogeneous catalyst is supported on a metallic or ceramic support which although may be neutral with respect to the chemical reactants contacting the catalyst, may have a physical or chemical effect on the catalytic components in immediate contact or approximate to the support. Thus, for catalytic converters, cordierite honeycombs are typically coated with one or more washcoats of catalytic layers. It is not uncommon for the cordierite substrate to alter the catalytic properties of the layer or layers in contact or proximate contact with the substrate such that differences between contemplated and actual results achieved with the catalyst may disadvantageously exist.

According to U.S. Pat. Nos. 6,063,633; 6,333,196; and 6,514,764, assigned to the University of Houston, Tex., a multisample holder (support) e.g., a honeycomb or plate, or a collection of individual support particles, is treated with solutions/suspensions of catalyst ingredients to fill wells in plates, or to produce cells, spots, or pellets, holding each of a variety of combinations of the ingredients, is dried, calcined or otherwise treated as necessary to stabilize the ingredients in the cells, spots, or pellets, then is contacted with a potentially reactive feed stream or bath, e.g., to catalyze biochemical reactions catalyzed by proteins, cells, enzymes; gas oil, hydrogen plus oxygen, ethylene or other polymerizable monomer, propylene plus oxygen, or $CC_{12}F_2$ and hydrogen. The reaction occurring in each cell is measured, e.g., by infrared thermography, spectroscopic, electrochemical, photometric, thermal conductivity or other method of detection of products or residual reactants, or by sampling, e.g., by multistreaming through low volume tubing, from the vicinity of each combination, followed by analysis, e.g., spectral analysis, chromatography, etc., or by observing temperature change in the vicinity of the catalyst, e.g., by thermographic techniques, to determine the relative efficacy of the catalysts in each combination. Robotic techniques can be employed in producing the cells, spots, pellets, etc. These patents disclose that the process can be used to form and analyze a variety of catalysts including those for chemical and hydrocarbon conversions. Supports such as inert clays, zeolites, ceramics, carbon, plastics, e.g., reactive plastics, stable, nonreactive metals, or combinations of the foregoing can be used. The catalyst candidate precursors can be deposited onto the supports by any convenient technique, preferably by pipette or absorbing stamp (like a rubber stamp), or silkscreen.

In accordance with copending, commonly assigned U.S. Ser. No. 10/118,185, filed Apr. 8, 2002, there is disclosed a process for the preparation and use of a substrate having multiple samples of composite compositions provided thereon. The composite samples comprise one or more components coated onto a substrate in discrete regions of the substrate or in continuous concentration gradients covering large sections of the substrate and varying in concentration along one or more axes of the substrate. The substrate, if desired, can comprise part of the composite.

Drying of the components placed on the substrate, if necessary, can take place simultaneously after application of each component or subsequent to application of the final component. After deposition of the components is complete, composite samples containing one or more components attached to the substrate can then be removed with or without the underlying substrate layer and screened for useful properties. As such, the invention provides methods for the parallel synthesis of large numbers of novel composites. Analysis can then be done on each removed composite sample.

In a particularly useful embodiment for providing the library of composite compositions as disclosed therein; one or more of the component coatings are formed as a continuous gradient across the whole of the substrate. The gradient can be with respect to concentration or loading of a particular component or may vary in compositional differences. By applying a coating gradient across the substrate, it is possible to generate a composite library that contains all of the intermediate compositions or concentrations between a desired compositional or concentration range. Samples with any specific composition within the desired range can be tested from such a library by going to a specific location on the substrate sheet and testing at such location or cutting out the sample from the coated sheet. Thus, libraries of composite compositions with an exhaustive range of compositions can be prepared for one-component as well as multi-component compositions. Several overlapping gradients can be prepared to mimic complex multi-dimensional phase diagrams.

The embodiment of the invention disclosed in U.S. Ser. No. 10/118,185, where continuous gradients of coatings are applied across the substrate are exemplified as the gradient moves across a two-dimensional square sheet. In one configuration, the loading of a deposited component is increased as the gradient moves across the x-axis of the substrate sheet. In this case the loading changes only along the x-axis. In the second configuration, the minimum loading occurs at the corner of the sheet and increases as a function of both x and y. The coatings with continuous gradient concentrations can be prepared as either single-component or multi-component systems. Examples of libraries with these gradient coatings include the following: (1) Uniform coatings of one or more components can first be placed on the substrate sheet. In such case the composition of the entire surface would be the same. Subsequent to the application of the uniform coating, one or more gradient coatings such as those described above could be placed on top of the base coat. (2) The configuration may be prepared as a single-component system to examine the effect of concentration of a particular component on a composite. Such a technique is even more powerful when two different gradients are placed on the same surface. The minimum loading for the first component can be at one corner of the sheet while the minimum loading for the second component may be at either a neighboring corner or at the opposite corner of the sheet to create different combinations of the two components. Alternatively, the patterns for the two components may overlap one another, i.e. the minimum for both would occur at the same corner. (3) The configuration can also be used to place two different gradient coatings. Three unique orientations of the second gradient relative to the first are possible: (a) the minimum loading of the second component occurs at the same location as the minimum of the first component, therefore as the gradients move across the sheet, loading for both components increase, (b) the minimum loading for the second component occurs at an edge that is adjacent to the edge for the minimum loading for the first component. Therefore, the two patterns are 90° off relative to each other. (c) The minimum loading for the second component occurs at an edge that is opposite of the edge of the minimum loading for the first component, and therefore, the two patterns are 180° off relative to each other. While the libraries are not limited in terms of the numbers of components that can be applied, the gradient technique is quite powerful to yield a vast number of composite compositions even when using only one or two deposited components. The configuration as described above are just a few of the possible ones which can be applied.

The use of screen printing is a particularly useful technique to form gradient coatings. The appropriate screen to deliver a gradient coating can be produced by photolithographic techniques known in the art.

Once the gradient coatings have been applied to the substrate in the desired manner, it is important to be able to calculate the composition of any given spot on the gradient based on its location. A mathematical protocol disclosed in U.S. Ser. No. 10/118,185 has been devised for determining these compositions depending upon the coating gradient protocol which has been used. The method as developed in this copending application for the placement of gradient coatings onto a ceramic sheet has enabled many combinations of two or more materials to be formed and tested and has greatly enhanced the combinatorial screening of heterogeneous catalysts. However, the method has not been as effective for generating libraries containing all possible combinations that add up to a constant total in combinatorial systems containing three or more components.

Regardless of the use of the composite, there is an increasing need to rapidly test different compositions, configurations of compositional layers and/or relative concentrations of components with respect to each other. Accordingly, an enormous need still exists with respect to testing the numerous possible combinations of multiple materials used to form a composite or new composition. The variables for making a composite or new composition are still huge even if each component of the composite or composition is known and selected inasmuch as the arrangement (configuration) of layers, if used, and/or concentration of the individual components with respect to the other components still need to be tested for the desired properties which are sought.

SUMMARY OF THE INVENTION

The present invention is directed to the preparation of "libraries" of composites or compositions. Large numbers of the composites or compositions can be screened to determine the effectiveness of the individual composite or compositions which are prepared.

The present invention provides methods for the preparation and use of a substrate having multiple samples of composites or compositions formed from reactive components provided thereon. The composites or compositions comprise one or more components coated onto a substrate in concentration gradients covering a section of the substrate and varying in concentration along one or more axes of the coated section. The substrate, if desired, can comprise a part of the composite. Such embodiment is particularly useful when the composite is a heterogeneous catalyst, since the carrier for the catalytic layers often affects catalytic properties.

In accordance with this invention, the libraries of the composites or compositions are provided by a technique in which one or more coatings in the form of concentration gradients are placed on the surface of a substrate. What is meant by "concentration" is the amount, e.g., weight or moles, of the component per unit area of the substrate. By such technique, an infinite number of point compositions are formed. Accordingly, the potential number of samples resulting from the formation of gradients across a substrate surface is much higher than in the approach in which the samples are formed in individual discrete regions, wells, or plates on a substrate. In this invention, the coating for a particular component of the composite or composition increases as the coating moves across the 2-dimensional substrate sheet. A particularly useful feature of the present invention is that the shape of the gradient on the substrate is in the form of a triangle. By applying the gradient coatings as triangles, three or more components for each composite or composition sample can be deposited in unique combinations of components which could not be readily achieved by applying gradient squares on a substrate surface. Once a desired composition range is defined, it is possible to generate a library that contains all of the intermediate compositions. Samples with any specific composition can be examined from the library by going to the appropriate location on the sheet. By utilizing the triangle as the shape of the gradient coating, the exact composition of each composite or composition sample can be readily obtained by borrowing from the triangular phase diagram which has been used for many years in the ceramic industry and is indispensable for calculating the crystalline phase of a composition of two or three materials.

DETAILED DESCRIPTION OF THE INVENTION

Figure 2:
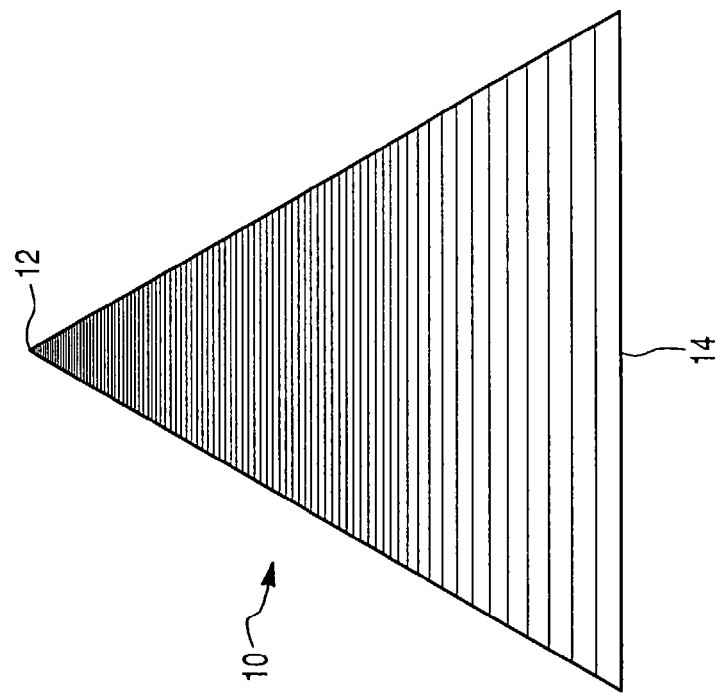
FIG. 2 is a depiction of one applied component in the form of a concentration gradient shaped as a triangle in accordance with the present invention.

In general, the present invention provides a method for the preparation of multiple samples of composites or compositions applied on a support surface. In a particular embodiment, the substrate becomes part of the composite sample. This particular embodiment is useful in testing heterogeneous catalyst samples, for example, since often the substrate, which carries the active catalytic layers, has an effect on catalytic properties. Heterogeneous catalysts with or without the underlying substrate can be individually tested for catalytic properties as well as other chemical, physical, and electrical properties. The heterogeneous catalyst samples are provided by coating one or more catalytic layers as concentration gradients of each respective layer onto the substrate whereby one discrete region of the substrate will have an overall catalyst composition comprising one or more layers of catalytic material which is different from the catalyst composition contained on other discrete regions of the substrate. The catalyst samples can be cut out from the discrete regions of the support as tablets and the individual catalytic tablets tested for desired properties.

The library of composites is not intended to be limited solely to forming samples of heterogeneous catalysts. Composite samples which are formed can be for any and all useful purposes. Additional non-limiting examples include catalysts, adsorbents, pigments, coatings, ceramics, glasses, sensors, electronic materials, optical materials, construction materials, molded plastic parts, etc.

Flat sheets made from a variety of materials can serve as a substrate for forming the library of composite components in the method of this invention. Thus, the sheets can be made of ceramics, such as oxides or silicates, including, for example, alumina, zirconia, etc., and cordierite; non-oxide ceramics such as metal carbides and nitrides; metals, such as, for example, stainless steel, aluminum, etc.; glass; polymers; and composites of the listed materials. Porous as well as dense materials can be utilized. It is most useful if the substrate, whether rigid or semi-rigid, can be cut or perforated so as to yield individual sample tablets subsequent to the coating process and which can be tested for properties as described above. It is preferred that the substrate used be one that is compatible with the components or layers that are delivered to the substrate and can be used effectively in the environment in which the composite is to be used. For example, cordierite sheets are especially preferred as a substrate for heterogeneous catalysts since cordierite is known as a support for catalytic layers such as in automotive catalytic converters. Thus, cordierite sheets provided with multiple samples of various catalytic layers can mimic honeycomb monoliths, which are used in automotive catalytic converters.

The composite components which are applied onto the substrate as gradient coatings are typically metals and metal oxides which can be coated onto the substrate in the form of a solid, liquid, slurry or solution, including inks, pastes, gels, suspensions, or vapor phase. The component can be deposited onto the substrate by various coating techniques such as spraying, immersion, pouring, rolling, vapor deposition techniques, etc. Aforementioned U.S. Pat. No. 5,985,356 discloses numerous techniques for applying reactive components to form a combinatorial array. Such techniques can be readily used herein to form a library of composite compositions.

The use of screen printing is a particularly useful technique to form gradient coatings. The appropriate screen to deliver a gradient coating can be produced by photolithographic techniques known in the art. The movement of a draw-down bar across a surface to vary the coating thickness, and gravure roll coating are additional methods that can be used to form coating gradients across the substrate surface.

The types of materials that can be applied as coatings include but are not limited to:

(a) Oxides of metals and main group elements, including transition metal oxides such as zirconia, titania, manganese oxide, rare earth oxides such as ceria and lanthanum oxide; binary, ternary, and more complex solid state oxides and ceramic phases; various forms of alumina, silica, aluminosilicates and aluminophosphates.

(b) Natural and synthetic forms of aluminosilicate and silicate zeolites such as ZSM-5, Beta, zeolite Y, and ferrierite, various forms of molecular sieves such as aluminophosphates and titanosilicates;

natural or synthetic clays and related minerals such as kaolin, attapulgite, talc, montmorillonite, and Laponite®.

(c) Non-oxide ceramics such as metal carbides and nitrides.

(d) Various forms of carbons such as activated carbon, carbon molecular sieves, graphite, fullerenes, carbon nanotubes, and carbon black.

(e) Various organic polymers, oligomers, or resins, such as polyethylene, polypropylene, polystyrene, polyamides, halo hydrocarbon polymers, polyesters, etc.

(f) Metals such as precious metals and/or transition metals deposited, mixed with, or exchanged into any support such as any of the materials described in (a)-(e) above. Examples of such phases include Pt/alumina, Pd/alumina, and Cu-ZSM-5.

The metals or metal oxides may also be initially applied as metal salts which can be reduced or oxidized to the desired metal or metal oxide layer. The types of metals, metal compounds or non-metallic components that can be applied are limited only to the extent of the periodic table of elements and accordingly, there are no further limitations as to the elements, compounds or polymers that can be used as components. It is this availability of vast numbers of materials and the indefinite combinations of the materials that can be prepared, especially when more than one composite component or layer is applied, that leads to the necessity and importance of finding a way of preparing and testing a vast library of composite samples.

If metals are to be applied to the substrate, deposition can be achieved from vapor deposition, powder or slurry of metal or metal oxides, supported metal or metal oxides, as well as the applications of metal salts dissolved in water or other solvent or metal salts impregnated onto carrier particles. The metal salts can be converted to metals or metal oxides by a subsequent reduction or oxidation step after application of the solution, or upon deposition of the metal salt/carrier particles and removal of the solvent or slurry mediums. A particular useful method of applying metals is to first impregnate or otherwise deposit a metal or metal salt on a porous carrier particle such as alumina. The metal/alumina particles can then be applied as gradients. Pt/alumina, Rh/alumina, or Pd/alumina are non-limiting examples of metal/carrier components. If the alumina carrier or other porous carrier is impregnated with metal salts, the metal salt/carrier coatings can then be treated subsequent to deposition to oxidize or reduce the various metal salts to metal oxides or metals, respectively. Treatment can be immediately after each layer is applied or after all layers of metal salts have been applied.

In the process of driving off solvents or liquid carriers and/or converting metal salts to metals or metal oxides by thermal treatment, it is important that such heat treatment is not so severe as to cause a substantial reaction between the individual metal components or layers with other components or layers. Thus, while two metals or metal salts may be applied, subsequent heat treatment should still yield two different metal compounds whether as pure metal or metal oxides. Substantial reaction between two metal components or oxides to form a third different metal, metal alloy, or oxide component is to be avoided in the forming of composite libraries. Thus, in forming composites, any treatment of the coated substrate should not yield a substantial reaction between deposited composite components. What is meant by not yielding a substantial reaction is that at least 80% wt. of the deposited layers or components should remain unreacted with any other deposited component or layer. Preferably, at least 90% of the deposited components or layers remain unreacted with other layers, and most preferably, greater than 95 weight percent of the deposited layers should remain unreacted with other deposited components or layers.

Evaluation of the composite samples may consist of any type of electronic, optical, physical, or chemical testing. For heterogeneous catalysts this involves contacting the sample with one or more reactive compounds at certain conditions (e.g. flow rate, concentration, temperature, contact time, etc.) and evaluating the extent and nature of the reactivity of one or more of the reactive compounds by techniques such as mass spectrometry, infra-red spectrometry, gas chromatography or any other suitable and useful method. Typically, properties of the catalyst such as activity, selectivity, stability, rate constants, activation energies etc. may be determined.

The present invention is also related to forming libraries of new compositions which are formed by application of two or more reactive components, as gradient coatings onto a substrate. Once the components of interest have been delivered as gradient coatings onto the substrate, the components can be reacted using a number of different synthetic routes to form an array of materials. The components can be reacted using, for example, solution based synthesis techniques, photochemical techniques, polymerization techniques, template directed synthesis techniques, epitaxial growth techniques, by the sol-gel process, by thermal, infrared, or microwave heating, by calcinations, sintering, or annealing, by hydrothermal methods, by flux methods, by crystallization through vaporization of solvent, etc. Thereafter, the compositions can be screened for materials having useful properties.

"Component" as used in forming compositional arrays is meant to refer to each of the individual chemical substances that act upon one another to produce a particular material and is otherwise referred to herein in the alternative as "reactant" or "reactant component." That is to say, the components or, alternatively, reactants are the molecules that act upon one another to produce a new molecule(s), i.e., product(s); for example, in the reaction HCl+NaOH→NaCl+H$_2$O, the HCl and the NaOH are the components or reactants.

For producing the composition samples, any reactive component can be utilized. Below are non-limiting examples of useful compositions that can be formed as compositional libraries of this invention. The compositions listed below include those disclosed in U.S. Pat. No. 5,985,356.

Ionic Solids: Solids which can be modeled as cations and anions held together by electrical attraction of opposite charge. Such ionic solids include, but are not restricted to, CaF$_2$, CdCl$_2$, ZnCl$_2$, NaCl$_2$, AgF, AgCl, AgBr, and spinels (e.g., ZnAl$_2$O$_4$, MgAl$_2$O$_4$, FrCr$_2$O$_4$, etc.).

Molecular solids: Solids consisting of atoms or molecules held together by intermolecular forces. Molecular solids include, but are not limited to, extended solids, solid neon, organic compounds, synthetic or organic metals (e.g., tetrathiafulvalene-tetracyanoquinonedimethae (TTF-TCNQ)), liquid crystals (e.g., cyclic siloxanes) and protein crystals.

Inorganic Materials: Materials which do not contain carbon as a principal element. The oxides and sulphides of carbon and the metallic carbides are considered inorganic materials. Examples of inorganic compounds which can be synthesized using the methods of the present invention include, but are not restricted to, the following:
(a) Intermetallics (or Intermediate Constituents): Intermetallic compounds constitute a unique class of metallic materials that form long-range ordered crystal structures below a critical temperature. Such materials from when atoms of two metals combine in certain proportions to form crystals with a different structure from that of either of the two metals (e.g., NiAl, CrBe$_2$, CuZn, etc.).
(b) Metal Alloys: A substance having metallic properties and which is composed of a mixture of two or more chemical elements of which at least one is a metal.
(c) Magnetic Alloys: An alloy exhibiting ferromagnetism such as silicon iron, but also iron-nickel alloys, which may contain small amounts of any of a number of other elements (e.g., copper, aluminum, chromium, molybdenum, vanadium, etc.), and iron-cobalt alloys.
(d) Ceramics: Typically, a ceramic is a metal oxide, boride, carbide, nitride, or a mixture of such materials. In addition, ceramics are inorganic, nonmetallic products that are subjected to high temperatures (i.e., above visible red, 540° C. to 1000° C.) during manufacture or use. Such materials include, for example, alumina, zirconium, silicon carbide, aluminum nitride, silicon nitride, the YBa$_2$Cu$_3$O$_{7-8}$ superconductor, ferrite (BaFe$_{12}$O$_{19}$), Zeolite A (Na$_{12}$[SiO$_2$]$_{12}$(AlO$_2$)]27H$_2$O), soft and permanent magnets, etc. High temperature superconductors are illustrative of materials that can be formed and screened using the present invention. "High temperature superconductors" include, but are not restricted to, the $La_{2-x}Sr_xCuO_4$ superconductors, the Bi$_2$CaSr$_2$Cu$_2$O$_{8+x}$ superconductors, the Ba$_{1-x}$K$_x$BiO$_3$ superconductors, and the ReBaCu superconductors. Such high temperature superconductors will, when they have the desired properties, have critical temperatures above 30° K, preferably above 50° K, and more preferably above 70° K.
(e) Zeolites prepared by various techniques
(f) Supported catalysts (metals deposited on a support)
Organic Materials: Compounds which generally consist of carbon and hydrogen, with or without oxygen, nitrogen, or other elements, except those in which carbon does not play a critical role (e.g., carbonate salts). Examples of organic materials which can be synthesized using the methods of the present invention include, but are not restricted to, the following:
(a) Non-biological, organic polymers: Nonmetallic materials consisting of large macromolecules composed of many repeating units. Such materials can be either natural or synthetic, cross-linked or non-crosslinked, and they may be homopolymers, copolymers, or higher-ordered polymers (e.g., terpolymers, etc.). By "nonbiological," a-amino acids and nucleotides are excluded. More particularly, "non-biological, organic polymers" exclude those polymers which are synthesized by a linear, stepwise coupling of building blocks. Examples of polymers which can be prepared using the methods of the present invention include, but are not limited to, the following: polyurethanes, polyesters, polycarbonates, polyethyleneimines, polyacetates, polystyrenes, polyamides, polyanilines, polyacetylenes, polypyrroles, etc.

Organometallic Materials: A class of compounds of the type R-M, wherein said carbon atoms are linked directly with metal atoms (e.g., lead tetraethyl (Pb(C$_2$H$_5$)$_4$), sodium phenyl (C$_6$H$_5$Na), zinc dimethyl (Zn(CH$_3$)$_2$), etc.).

The new compositions that are formed can be screened for properties such as, for example, electrical, thermal mechanical, morphological, optical, magnetic, chemical, etc. More particularly, properties which can be screened include, for example, conductivity, superconductivity, resistivity, thermal conductivity, anisotropy, hardness, crystallinity, optical transparency, magnetoresistance, permeability, frequency doubling, photoemission, coercivity, critical current, or other useful properties which will be apparent to those of skill in the art upon review of this disclosure. Importantly, the synthesizing and screening of a diverse array of materials enables new compositions with new physical properties to be identified. Any material found to possess a useful property can be subsequently prepared on a large scale. It will be apparent to those of skill in the art that once identified using the methods of the present invention, a variety of different methods can be used to prepare such useful materials on a large or bulk scale with essentially the same structure and properties.

Figure 1:
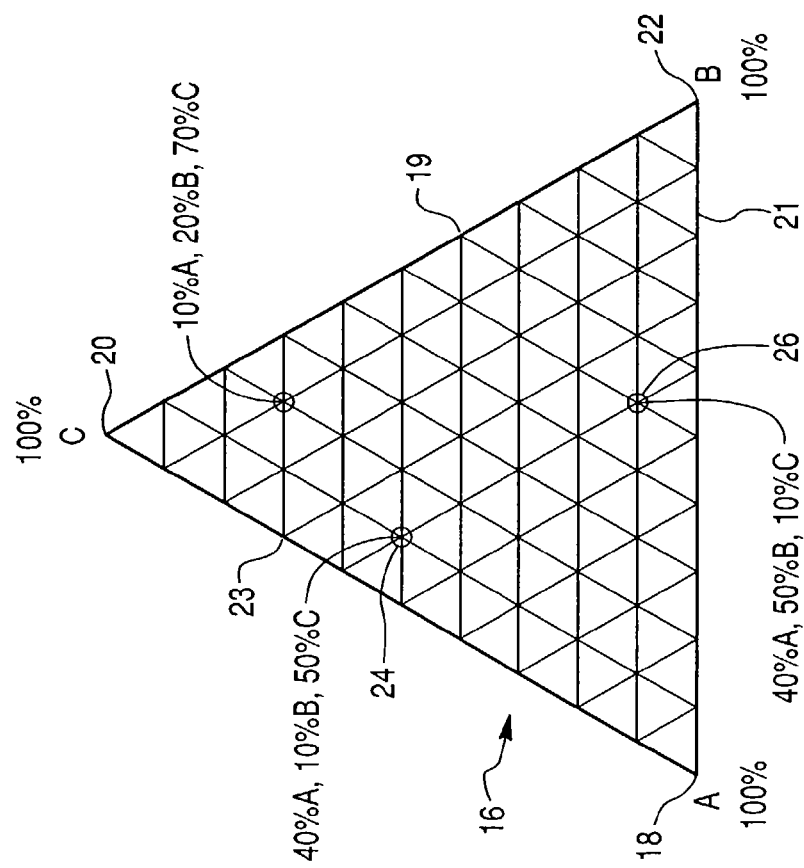
FIG. 1 is a simulated phase diagram used in calculating the crystalline phase composition of a ceramic containing components A, B, and C.

In accordance with the present invention, the libraries of composites or novel compositions are formed by applying each component as a gradient coating on the substrate in the form of a triangle. The gradient coating of each component, whether to form a composite or a novel composition, is exemplified in FIG. 2. As shown in FIG. 2, a gradient coating, in the form of a triangle 10, has the greatest concentration of the component at the apex 12 of triangle 10. It is preferred that the concentration of the component applied onto a surface uniformly decreases from apex 12 to base 14 of triangle 10. As will be shown below, the application of the components as gradients in the shape of triangles allows a sample to be prepared from three components in which every relative concentration of the three components that add up to a constant total are provided within the triangle. Importantly, the relative concentration of the three components at any sampled section of the triangle can be readily obtained. The ability to readily determine the relative concentrations of the three components applied as gradient coatings in the shape of triangles on the substrate is analogous to the determination of the respective concentrations of a three component ceramic with a triangular phase diagram which has been used to depict ceramic compositions for many years. Such a phase diagram is shown in FIG. 1, in which phase diagram 16 represents a mixture of three components A, B, and C in which at the labeled apexes of the triangle, 100% of the respective component is present. Thus, the concentration of component A from apex 18 to side 19 decreases from a concentration of 100% A to 0% A. Likewise, the concentration of component C from apex 20 to side 21 decreases from 100% C to 0% C. The concentration of component B ranges from 100% at apex 22 to 0% at side 23. The relative percentages of components A, B, and C at any sampling area of the phase diagram 16 can be readily determined. For example, as shown, the relative concentration of the components at sampling area 24 is 40% A, 10% B, and 50% C, while at sampling area 26, a composition comprising 40% A, 50% B, and 10% C is shown.

Phase diagram 16 is well known and has been used in the literature, including patent literature, to define the components of a ceramic composition. This concept has been now used in preparing composite and compositional libraries of three or more components and allows for all possible combinations that add up to a constant total of three components to be configured in the shape of a triangle on a substrate.

Preferably, a screen printing method is utilized to deposit the various components as gradients in the form of triangles. The screen printer typically uses a squeegee to force the components through a screen. The screen is designed to allow the component material to pass through the openings of the screen arranged in a predetermined shape according to the application. No material passes through those parts of the screen that are blocked off by design, using an impervious polymer or similar material. The material forced through the screen onto the substrate surface can be, for example, in the form of a screen printing ink.

A screen printing ink is defined as a specific formulation consisting of a powder (for example, a catalyst component or reactive material) or liquid component, a carrier solution or solvent, and, optionally, a few additives that result in a product with high-quality screen-printing properties. A carrier is defined as a suspending agent for the solid component of a screen printable ink or solvent to disperse any liquid component, reactive or non-reactive. The carrier typically makes up the bulk of the key properties of an ink and generally defines the viscosity and tackiness. The key properties of an ink formulation are the viscosity, and the component loading. In order to form a good coating, inks are required to have a high viscosity, similar for example to a thick honey. If the viscosity is too high, the ink will not distribute itself across the screen properly for an even and well-distributed print. Likewise, if the viscosity of the ink is too low, the print quality also suffers since the ink will not distribute itself properly across the screen during the printing and may result in smearing of the desired pattern.

Typical particle sizes of the starting powder range from 2 μm to 50 μm. The ink goes through a blending and milling process, which reduces the particle size down to 1-25 μm. Typically screens are made of polyester or stainless steel monofilaments woven into a grid pattern. Monofilament diameters range from 0.6 mils (or 15 μm) up to 15.2 mils (or 385 μm).

As the ink is forced through the screen by the squeegee, what is left behind is a well-defined, uniform layer in the same shape as the openings on the screen. Typically, the layer of each component left on the substrate is 15 to 25 microns. The thickness can be varied by altering the solids content and/or viscosity of the component ink. The thickness can also be varied by adjusting the height of the impervious component in the screen.

A typical gradient coating in the form of a triangle, such as triangle 10 in FIG. 2, corresponds to a six-inch equilateral triangle which has a 5.2 inch height. Obviously, triangles of different sizes as that exemplified can be used. The particular size of the applied triangle is not deemed to be particularly critical. The gradient concentration runs from the highest concentration at apex of 12 to the side 14 opposite apex 12. The gradient is defined by an exposure or opening in the printing screen that is gradually decreased along the axis or height of the triangle from apex 12 to base 14. As shown in FIG. 2, the gradient was made to run from 100% exposure, which means the maximum amount of component material is allowed to flow through the screen at apex 12 to a 0% exposure in which no component material is allowed through at base 14. The rate of concentration change is not critical, although the rate of change per linear height of the triangle should be as small as possible to allow for a greater range of component variability. A rate of change of 1% per hundredth of the distance from apex 12 to base 14 is useful, for example. Accordingly, a point that is halfway between the apex 12 and base 14 represents a 50% loading level of the component material on the substrate. While FIG. 2 illustrates a gradient concentration of from 100% to 0%, it is understood that other sets of gradients could be formed, such as from 50-100%, 60-80%, etc., to allow further examination of more specific combinations of component materials.

Figure 3:
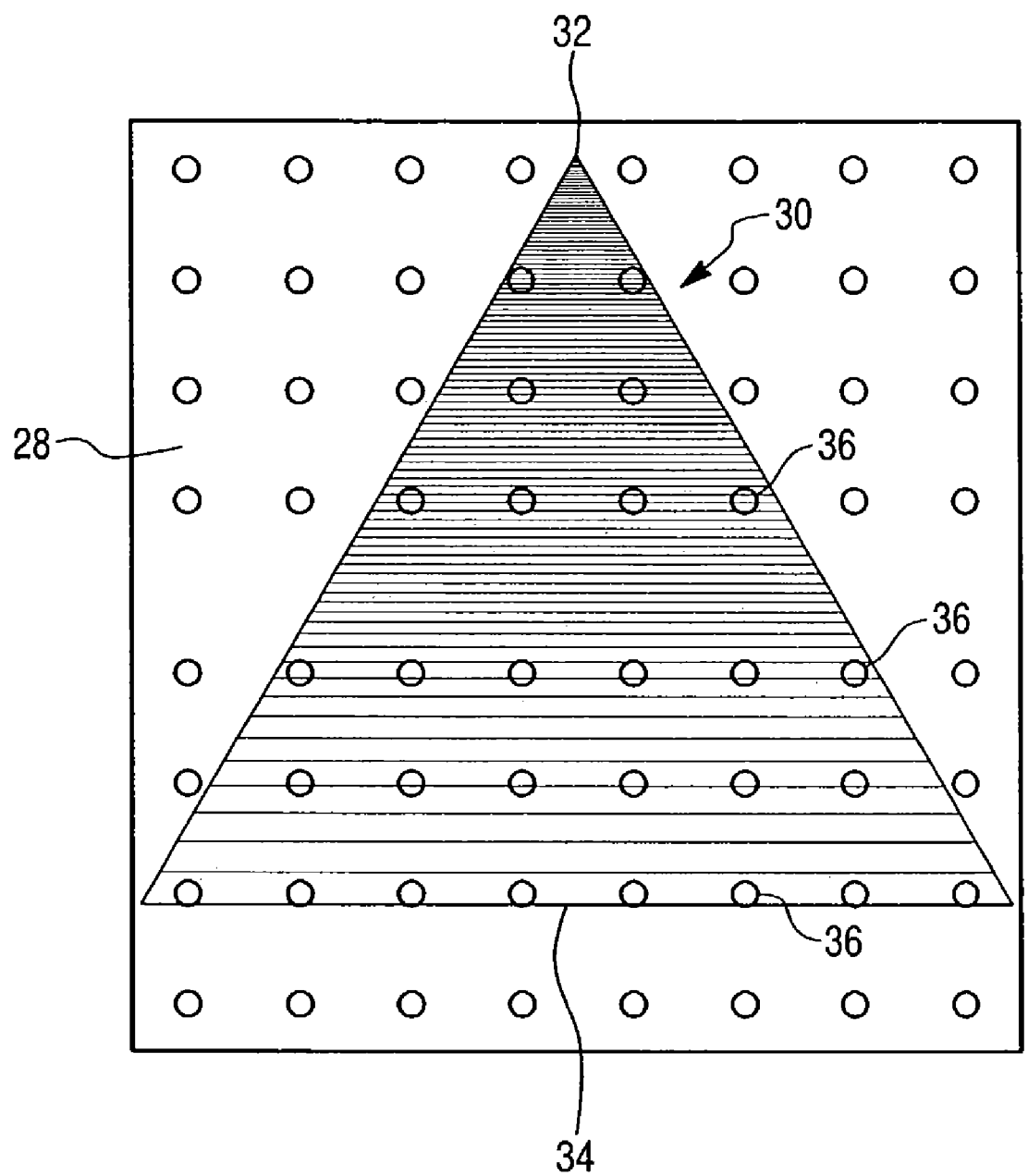
FIG. 3 depicts a pre-cut substrate which has been coated with a component as a concentration gradient shaped as a triangle in accordance with this invention.

In FIG. 3, a concentration gradient of a component is deposited onto a pre-perforated cordierite sheet 28 in the form of triangle 30. The concentration of the applied component is at a maximum at apex 32 and a minimum at base 34 of triangle pattern 30. The circled portions indicated by reference numeral 36 spaced across substrate 28 are precut portions of the cordierite substrate which allow the sample, along with the underlying substrate, to be removed and tested. Such a sheet is particularly useful for catalyst composites in as much as the carrier for the component materials often has an effect on catalytic properties.

A method of forming and perforating ceramic sheets into precut substrates is disclosed in aforementioned, co-pending U.S. Ser. No. 10/118,185, the entire content of which is herein incorporated by reference. As disclosed therein, such substrate sheets may be formed from a roll of tape cast ceramic such as cordierite, which roll is provided with perforations across the width thereof and spaced along the length of the roll to divide the roll into a plurality of individual substrate sheets. The sheets are eventually cut along the perforations into separate substrate sheets. A tape cast ceramic contains a ceramic phase and a binder, such as a polymer or other binder source. The binder is burned off upon firing to provide the pure ceramic sheet. Prior to heat treatment, the tape cast ceramic sheets are relatively soft and are able to be cut or perforated by a sharp device. The separated sheets are stacked one on top of the other and while still containing binder, a sharp device can be pressed into the sheet, e.g. a cylindrical tube with a sharp edge would result in a perforated circle as indicated by reference numeral 36 in FIG. 3. A plurality of these perforations 36 can be formed throughout the surface of the substrate sheet 28. An underlying substrate sheet can act as a base layer so as to hold the perforated sections 36 in place within substrate sheet 28 prior to and during the coating process. Once the tape cast sheet is perforated, the sheet is fired to remove the binder, harden and densify the substrate sheet. Subsequent to firing, one or more coating layers can be applied to the top surface of the substrate by the methods described above.

Figure 4C:
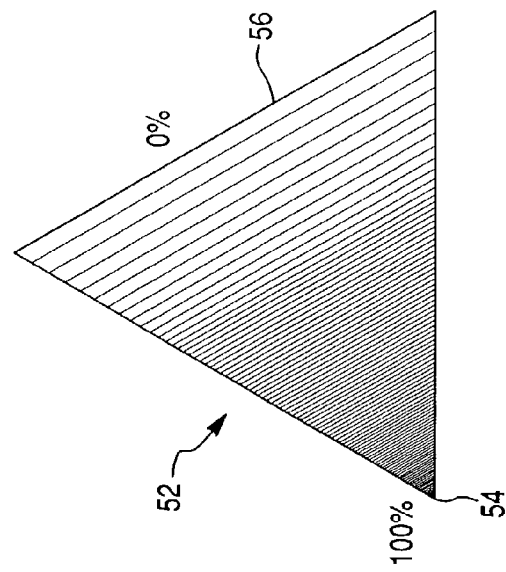
FIGS. 4A, B, and C illustrate how a three component composite or composition can be formed using the triangular gradients of the present invention.
Figure 4B:
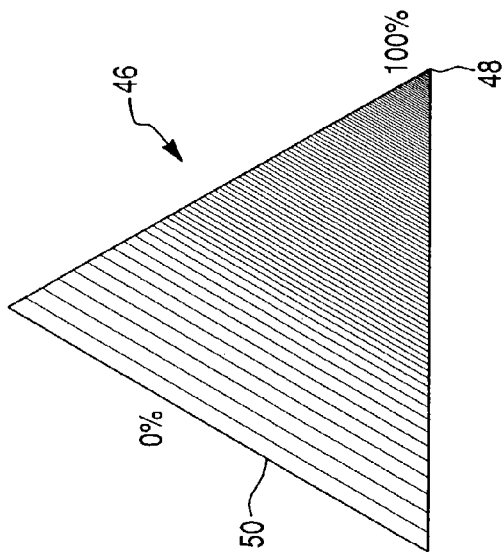
Figure 4A:
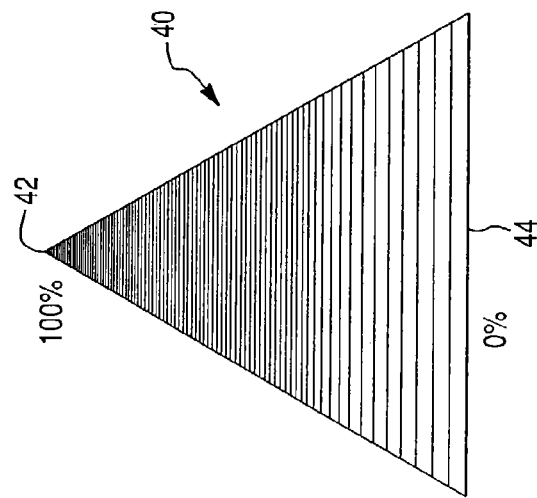

FIGS. 4A, B, and C illustrate how the gradient pattern as disclosed in FIG. 2 can be manipulated to form a 3-way gradient pattern when three components, A, B, and C, are applied onto the substrate. The 3-way gradient pattern is formed by depositing three overlapping triangles which are offset by a 120° rotation.

Referring to FIG. 4A, it can be seen that component A is applied as a gradient coating in the form of a triangle 40. The concentration of component A is at a maximum at apex 42 of the triangle, and is at a minimum or 0% at base 44 of triangle 40. The concentration of component A from apex 42 to base 44 of triangle 40 decreases in a uniform manner. Thus, the concentration decreases at a constant rate per unit height of triangle 40. In this way, a calculation of the composition at any point on the triangle 40 can be readily determined.

To apply a second gradient coating, the same screen used to apply coating A or an equivalent screen can be used wherein the apex of the triangular screen in which the maximum amount of coating is applied is rotated 120° from that shown in FIG. 4A. This is shown in FIG. 4B, wherein the gradient coating in the form of triangle 46 has its apex 48 which contains the maximum concentration of component B rotated 120° to the right relative to triangle 40. Base 50 of gradient triangular coating 46 contains the minimum or 0% of component B. Application of a third component C operates in the same manner, where again the triangular screen is rotated 120° such that the apex or maximum amount of coating is rotated 120° from the apex 48 of triangular coating 46. Thus, in FIG. 4C, triangular gradient coating 52 has its apex 54, which contains the maximum of component C rotated 120° from apex 48. Base 56 of triangle 52 contains the minimum amount or 0% of component C. When triangular gradient coatings 40, 46, and 52 are superimposed upon each other, what results is a triangle which contains at each corner the maximum or 100% of the respective components A, B, and C. This is equivalent to the ceramic phase diagram in FIG. 1. Thus, upon superimposing triangles 40, 46, and 52, the complete pattern would be an equilateral triangle where the three corners contain only 100% of one of the three components, and any other point on the triangle would have a combination of the three components that add up to 100% of the total. For example, a point in the exact center of the triangle would have 33.33% of each of components A, B, and C. This allows for removal and/or testing of samples that have every possible combination of the three components that add up to the equivalent of 100%. Offsetting the application of the gradient coatings as individual triangles may be used to obtain samples that contain an excess or shortfall of the components in order to determine the role of such compositions.

Although screen printing as disclosed is a very useful technique for forming the gradient coatings, the delivery of the components as continuous gradients across the surface of the substrate can be achieved by several other methods. One such method is a spray-coating process. A spray gun is oriented at an angle relative to the target and at one end of the target, thus resulting in higher coating loadings at locations closer to the spray gun and decreasing loadings with increasing distance. An additional approach takes advantage of a fine mesh screen that is placed between the spray gun and the target. Some of the coating remains on the screen and thus, does not reach the target creating the concentration gradients. By placing the screen at an angle relative to the gun, varying amounts of the coating are blocked by the screen depending on location and a gradient loading is generated on the target. Relative movement and varying the speed of the movement between the spray gun and target may be achieved using a variable speed motor to deliver gradient coatings. In each of the above cases, the substrate can be masked so that the exposed substrate is in the form of a triangle. Vapor coating techniques can also be used in combination with screens produced by photochemical methods to produce the concentration gradients.

Figure 5:
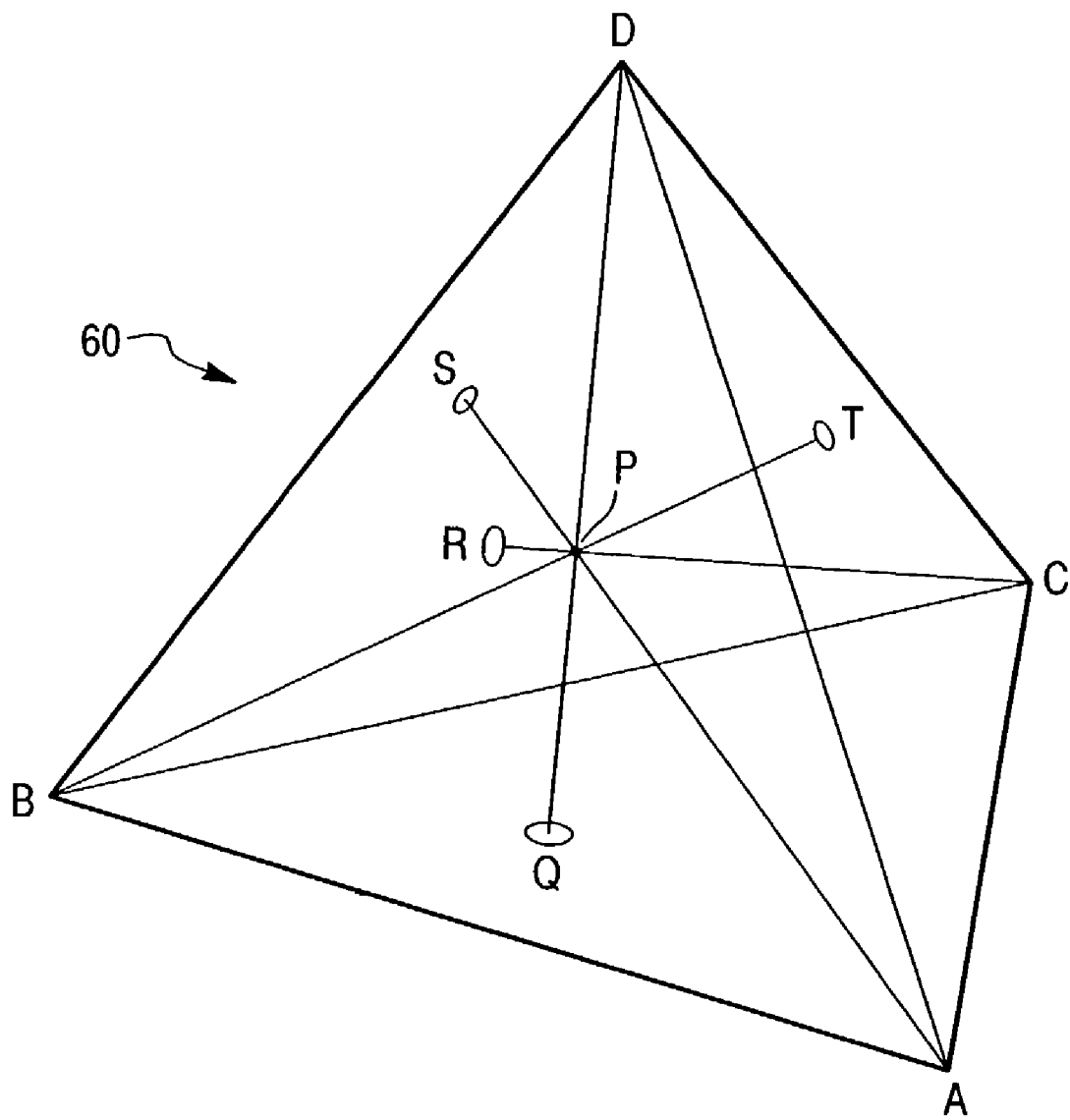
FIG. 5 is a depiction of a quaternary or four-way phase diagram in which a pyramid is used to correspond to a sample containing four components and illustrates how the amounts of A, B, C, and D can be determined for a sample P.

In addition to the three-way coatings and three-way phase diagrams, as shown in FIGS. 4A, B, and C, it is also possible to add a fourth component and form a quaternary or four-way phase diagram and readily calculate the relative concentration of the four components. Shown in FIG. 5 is a quaternary phase diagram which illustrates the manner of calculating the relative concentrations of components A, B, and C when a D component is also applied as a uniform coating and at a known concentration relative to the other components. The quaternary phase diagram 60 is a pyramid with a triangular base, and wherein each point on the pyramid corresponds to one of the four components A, B, C, and D. With component D being applied as a uniform coating, and not as a concentration gradient, the composition of a point within the pyramid for the other three components A, B, and C can be readily obtained. Thus, as shown in FIG. 5, to find the composition of a point P within the pyramid, lines from each of the four corners of the pyramid are drawn to the point, and the ratios of the line segments can be used to determine the composition at that point. For example, in FIG. 5, the relative amount of component A in sample P in pyramid 60 is the ratio of line segment P-S to line segment A-S. It is to be understood that the fourth component could be added as a gradient coating, and as long as the gradient coating is at a known concentration and known concentration gradient, a mathematical model can be developed to calculate the concentration of components A, B, C, and D anywhere within the pyramid. Obviously, additional coatings can be applied to provide more complex composite samples or provide additional reactive components for more complex compositions. It is believed possible to develop mathematical models which would be able to calculate the relative concentration of the components if such complex sampling is desired.

FIGS. 6(A-E) and FIGS. 7(A-E) are another way of illustrating four-phase diagrams in which components A, B, and C are applied as gradient coatings as shown in FIGS. 4(A-C) and a fourth coating D is applied as a uniform layer. The uniform layer D can be applied before or after the gradient coatings have been applied, or in between any two of the gradient coatings. In FIGS. 6(A), (B), and (C), components A, B, and C are applied as gradient coatings in the form of equilateral triangles as in FIG. 4. For each component, a maximum coating is applied at the different corners or apexes of the triangle, and a minimal, for example, zero, amount of coating is applied at the opposite base from each respective apex. In FIG. 6(D), what is illustrated is that the fourth coating is not deposited. This is further illustrated in FIG. 6(E) as a pyramid 62 in which the base 64 of the pyramid represents the 0% level of component D.

Figure 6A:
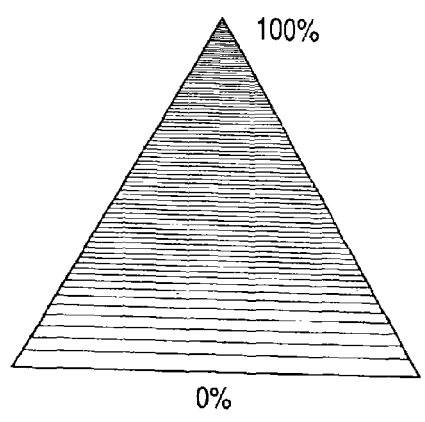
FIGS. 6(A-D) illustrate the application of four respective components on a substrate and FIG. 6(E) depicts how a quaternary phase diagram can represent the synthesized sample.
Figure 6B:
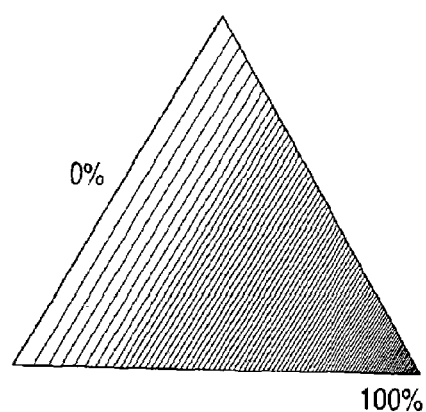
Figure 6C:
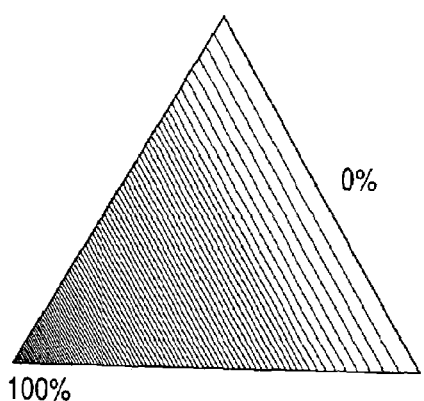
Figure 6D:
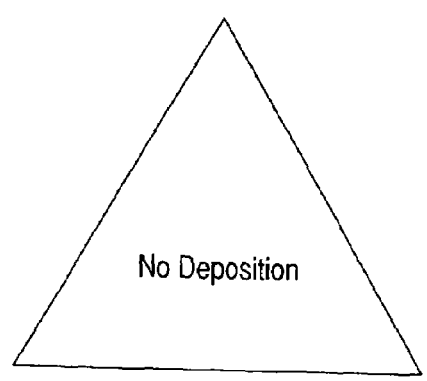
Figure 6E:
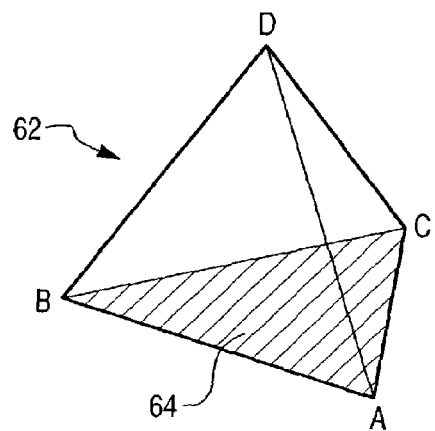
Figure 7A:
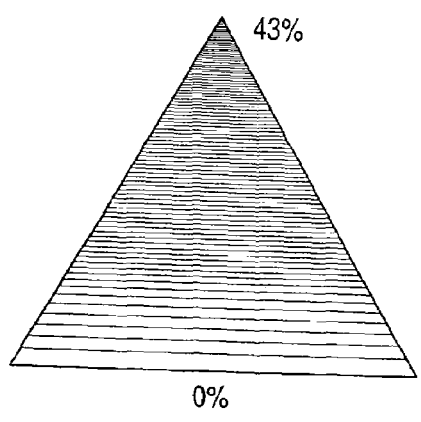
FIGS. 7(A-D) illustrate the application of four respective components on a substrate and FIG. 7(E) depicts how a quaternary phase diagram can represent the synthesized sample.
Figure 7B:
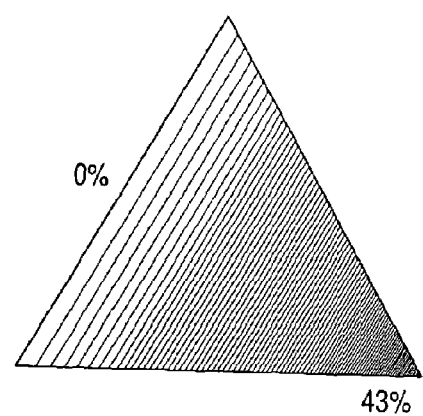
Figure 7C:
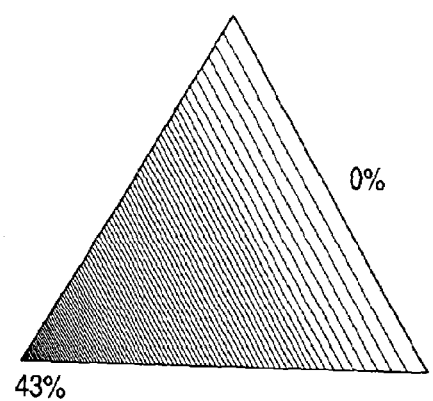
Figure 7D:
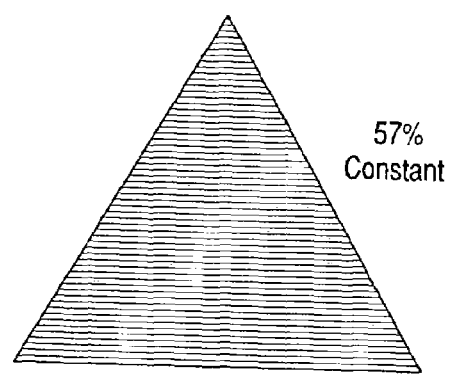
Figure 7E:
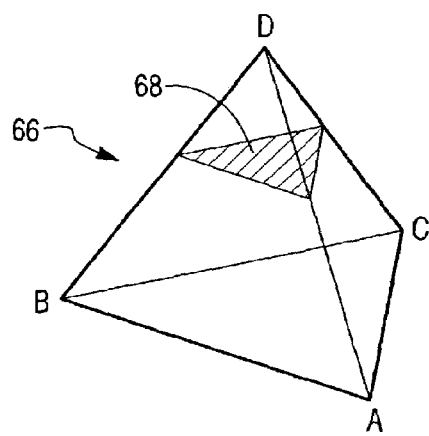

In FIG. 7, and in particular FIG. 7(D), what is shown is a fourth coating layer which is applied as a uniform layer that contains component D at a concentration of 57% relative to the total of component D and the maximum amount of any component A, B, or C. Components A, B, and C are applied as gradient coatings as shown in respective FIGS. 7(A-C). In this instance, the respective apexes of the deposited triangles for each component would be at a maximum concentration of 43% relative to the total concentration of the respective component A, B, or C and component D. FIG. 7(E) illustrates a pyramid 66 which represents the superimposition of the triangles of FIG. 7(A-C) and applied component D. Thus, in pyramid 66 the sample depicted in FIGS. 7(A-D) is represented by slice 68. Slice 68 represents a sample containing 57% concentration of component D and 43% of components A, B, and C at apexes 70, 72, and 74 respectively. As can be seen, slice 68 is moved from the base 76 or 0% component D as shown in FIG. 6(E). A pyramid as shown in FIG. 7(E) can be changed to represent any relative coating concentration of component D to the other components A, B, and C by illustrating any slice from the pyramid. For example, a slice of the pyramid at exactly point D would represent a single uniform coating of D with 0% of other coating components, which is opposite from FIG. 6(E) wherein the slice was taken at the base, or 0%, D. Thus, all combinations of components A, B, C, and D that add up to a constant total can be illustrated by the pyramid as shown in FIGS. 6 and 7 wherein the amount of the fourth component D is deposited uniformly onto the substrate sheet. Slices of 4-component combinations with specific target concentrations of each component, similar to FIG. 7D, can be experimentally prepared by either adjusting the ink compositions or the screen properties for each coating.

EXAMPLES

Example 1

3-Way Phase Diagram Printing

After a set of cordierite sheets was calcined, a screen printer was utilized to deposit a series of catalyst inks onto a single sheet. The screen used had a gradient pattern in the shape of an equilateral triangle with 6" long sides. First, an ink containing 2% Pd supported on stabilized zirconia was deposited. The weight of ink deposited was 0.11 g as-is, which, when dried at 90° C. for ½ hour, resulted in 0.0486 g of a dry coating. The substrate was then rotated 120° clock-wise on the screen printer. The next ink deposited contained an stabilized zirconia powder containing 2% Rh. The weight of ink deposited was 0.1134 g as-is, which, when dried at 90° C. for ½ hour, resulted in 0.0497 g of a dry coating. The substrate was then rotated another 120° clock-wise on the screen printer. The next ink deposited contained an stabilized zirconia powder containing 2% Pt. The weight of ink deposited was 0.1147 g as-is, which, when dried at 90° C. for ½ hour, resulted in 0.0427 g of a dry coating.

Using the solids content values of the inks from previous calcinations, the amount of solids from each ink were 0.0424 g, 0.0393 g, and 0.0399 g, respectively. This gives a ratio of components in the order of 1.05:0.97:0.99, which is extremely close to the desired value of 1.00:1.00:1.00.

Coating quality was excellent, with extremely sharply defined borders and no intrusion into other areas.

After the sheet had been calcined to 540° C. for 2 hours, samples were removed for analysis. The removal of pellets was performed by using a diamond-tipped coring drill bit with an inside diameter of 4.0 mm. Since the coating thickness is uniform throughout the triangular pattern, one is then able to divide the pattern into 100 rows of varying lengths, parallel to one edge and terminating at the apex. Based on the total weight of the sample deposited, the relative weight of a given row can be determined on the exposure level and length of the row. From this information, the loading of a single sample can be determined by applying the same formula for all the coatings present. Spreadsheets have been constructed to automate the calculations.

For the above example and the loadings present, and using the lower left corner (where 2% Rh/stabilized zirconia is at a maximum) as an origin in an XY-coordinate system, one can obtain a pellet containing 0.001 mg of 2% Pd/stabilized zirconia, 0.002 mg of 2% Rh/stabilized zirconia, and 0.063 mg of 2% Pt/stabilized zirconia by removing a sample from 5.75" on the X-axis, and 0.15" on the Y-axis. By removing a sample from 2.95" on the X-axis and 1.10" on the Y-axis, the resulting pellet contains 0.014 mg of 2% Pd/stabilized zirconia, 0.031 mg of 2% Rh/stabilized zirconia, and 0.026 mg of 2% Pt/stabilized zirconia.

Example 2

3-Way Phase Diagram Printing

After a set of cordierite sheets was calcined, a screen printer was utilized to deposit a series of catalyst inks onto a single sheet. The screen used has a gradient pattern in the shape of an equilateral triangle with 6" long sides. First, an ink containing 2% Pd supported on stabilized zirconia was deposited. The weight of ink deposited was 0.102 g as-is, which, when dried at 90° C. for ½ hour, resulted in 0.0451 g of a dry coating. The substrate was then rotated 120° clock-wise on the screen printer. The next ink deposited contained an stabilized zirconia powder containing 2% Rh. The weight of ink deposited was 0.1038 g as-is, which, when dried at 90° C. for ½ hour, resulted in 0.045 g of a dry coating. The substrate was then rotated another 120° clock-wise on the screen printer. The next ink deposited contained an stabilized zirconia powder containing 2% Pt. The weight of ink deposited was 0.1007 g as-is, which, when dried at 90° C. for ½ hour, resulted in 0.0382 g of a dry coating.

Using the solids content values of the inks from previous calcinations, the amount of solids from each ink were 0.0484 g, 0.0443 g, and 0.0440 g, respectively. This gives a ratio of components in the order of 1.06:0.97:0.97, which is extremely close to the desired value of 1.00:1.00:1.00.

Coating quality was excellent, with extremely sharply defined borders and no intrusion into other areas.

Samples from this sheet were removed in a fashion identical to Example 1. For the above example and the loadings present, and using the lower left corner (where 2% Rh/stabilized zirconia is at a maximum) as an origin in an XY-coordinate system, one can obtain a pellet containing 0.001 mg of 2% Pd/stabilized zirconia, 0.001 mg of 2% Rh/stabilized zirconia, and 0.056 mg of 2% Pt/stabilized zirconia by removing a sample from 5.75" on the X-axis, and 0.15" on the Y-axis. By removing a sample from 2.16" on the X-axis and 2.13" on the Y-axis, the resulting pellet contains 0.025 mg of 2% Pd/stabilized zirconia, 0.030 mg of 2% Rh/stabilized zirconia, and 0.009 mg of 2% Pt/stabilized zirconia.

Example 3

3-Way Phase Diagram Printing with 3 Layers of Each Component

After a set of cordierite sheets was calcined, a screen printer was utilized to deposit a series of catalyst inks onto a single sheet. The screen used has a gradient pattern in the shape of an equilateral triangle with 6" long sides. First, an ink containing 2% Pt supported on stabilized zirconia was deposited a total of three times. In between each coating, the substrate was dried at 90° C. for ½ hour. The weight of ink deposited for each layer was 0.0982 g, 0.1192 g, & 0.1158 g as-is, which, after drying, resulted in 0.0446 g, 0.0463 g, & 0.0505 g of a dry coating, respectively. The substrate was then rotated 120° clock-wise on the screen printer. The next ink deposited (in the same fashion) contained an stabilized zirconia powder containing 2% Rh. The weight of ink deposited for each of the layers was 0.1198 g, 0.1184 g, & 0.1151 g as-is, which, when dried at 90° C. for ½ hour between each coating, resulted in 0.0537 g, 0.0548 g, & 0.0526 g of a dry coating. The substrate was then rotated another 120° clock-wise on the screen printer. The next ink deposited (in the same fashion as the first) contained an stabilized zirconia powder containing 2% Pd. The weight of ink deposited was 0.1141 g, 0.108 g, & 0.1047 g as-is, which, when dried at 90° C. for ½ hour between each coating, resulted in 0.0519 g. 0.0465 g, & 0.0399 g of a dry coating.

Using the solids content values of the inks from previous calcinations, the total amount of solids from each ink were 0.1246 g, 0.1509 g, and 0.1259 g, respectively. This gives a ratio of components in the order of 0.93:1.13:0.94, which is very close to the desired value of 1.00:1.00:1.00.

Coating quality was excellent, with extremely sharply defined borders and no intrusion into other areas.

Samples from this sheet were removed in a fashion identical to Example 1. For the above example and the loadings present, and using the lower left corner (where 2% Rh/stabilized zirconia is at a maximum) as an origin in an XY-coordinate system, one can obtain a pellet containing 0.002 mg of 2% Pd/stabilized zirconia, 0.010 mg of 2% Rh/stabilized zirconia, and 0.182 mg of 2% Pt/stabilized zirconia by removing a sample from 2.91" on the X-axis, and 4.87" on the Y-axis. By removing a sample from 2.06" on the X-axis and 3.43" on the Y-axis, the resulting pellet contains 0.002 mg of 2% Pd/stabilized zirconia, 0.076 mg of 2% Rh/stabilized zirconia, and 0.129 mg of 2% Pt/stabilized zirconia.

Example 4

3-Way Phase Diagram Printing onto Flat Coating

This example, to be performed in a laboratory setting, involves coating a sheet of calcined cordierite with a uniform (10-25 um) layer of a catalytic ink that covers an area approximately 6"×6" square. The sheet will be dried at 90° C. for ½ hour. Then, a phase diagram containing 3 inks, similar to the previous Examples, will be printed onto the same sheet.

The goal of this example is to explore segments of a ternary phase diagram consisting of 4 components. By producing sheets using the above method, one is able to analyze single layers, or "slices" of the 4-way ternary diagram pyramid. This is useful to explore the possible effects and interactions that four individual components may have on each other in a catalytic role.

What is claimed is:

1. A method of producing a library of composite or composition samples on a substrate sheet comprising: depositing one or more components on said substrate sheet in the shape of an equilateral triangle, at least one of said components being deposited in the form of a continuous concentration gradient, forming test samples by removing portions of said triangle less than the whole of said triangle, an area of said portions having a concentration gradient of said at least one component and testing said samples for properties.

2. The method of claim 1, wherein said samples are removed from said substrate sheet by cutting said samples along with said underlying substrate from said substrate sheet.

3. The method of claim 2 wherein said samples are composites.

4. The method of claim 3, wherein said composites removed from said substrate sheet are heterogeneous catalysts.

5. The method of claim 1, wherein said components are deposited as a dry solid or as a solid contained within a liquid carrier onto said substrate sheet.

6. The method of claim 1, wherein at least one of said components is deposited from a slurry of said component in a liquid carrier.

7. The method of claim 1, wherein at least one of said components is deposited from a solution of such component within a solvent.

8. The method of claim 1, wherein at least one of said components is deposited onto said substrate sheet by a screen-printing process.

9. The method of claim 1, wherein at least one of said deposited components is in the form of a metal salt, elemental metal, metallic oxide, metal oxide ceramic, non-oxide ceramic or carbon.

10. The method of claim 3, wherein at least one of said deposited components is a hydrocarbon-based polymer.

11. The method of claim 1, wherein said sample is a composition and said deposited component is a reactive hydrocarbon-based monomer.

12. The method of claim 1, wherein said substrate sheet is selected from metal, ceramic, glass, polymer or composite of at least two of said components.

13. The method of claim 12, wherein said substrate sheet is cordierite.

14. The method of claim 12, wherein said substrate sheet is alumina, aluminum or stainless steel.

15. The method of claim 1, wherein at least two components are deposited onto said substrate sheet in a continuous concentration gradient patterned as an equilateral triangle, an area of said portions having a concentration gradient of said at least two components.

16. The method of claim 15, wherein:
a) said at least two components are superimposed on a single equilateral triangle pattern, and
b) for each component, the concentration is highest at one apex of said triangle pattern and lowest at a base opposite said apex.

17. The method of claim 1, wherein each of three components is deposited onto said substrate sheet in a continuous concentration gradient patterned as an equilateral triangle, an area of said portions having a concentration gradient of said at least three components.

18. The method of claim 17, wherein:
a) each of said three components are superimposed on a single equilateral triangle pattern, and
b) for each component, the concentration is highest at one apex of said triangle pattern and lowest at a base opposite said apex.

19. The method of claim 18, wherein at least one additional component is uniformly deposited on said substrate sheet and superimposed with the three components deposited as continuous concentration gradients.

20. The method of claim 19, wherein said at least one additional component is deposited before, after, or in-between deposition of said three components deposited as concentration gradients.

21. The method of claim 1 wherein said sample is a catalyst, adsorbent, or pigment.

22. The method of claim 17 wherein said sample is a catalyst, adsorbent, or pigment.

23. The method of claim 20 wherein said sample is a catalyst, adsorbent, or pigment.

24. The method of claim 3 comprising: cutting the substrate sheet so as to provide said sheet with a plurality of cut shaped portions which are spaced from each other on the surface of the sheet, depositing said at least one component on the surface of said sheet whereby the cut shaped portions of said sheet are covered by at least one of said deposited components, and removing said covered cut shaped portions of said sheet to form composite samples, said composite samples comprising said substrate containing at least one deposited component thereon in the form of said shaped portion, testing said composite samples for properties.

25. The method of claim 24, wherein said substrate sheet is a ceramic.

26. The method of claim 25, wherein said ceramic is cordierite.

27. The method of claim 24, wherein said cut shaped portions are still attached to said substrate sheet, said composite samples being removed from said sheet by applying pressure to said cut shaped portions.

28. The method of claim 24, wherein said cut shaped portions are formed from perforations made on the surface of said substrate sheet.

29. The method of claim 16 wherein said lowest concentration is 0%.

30. The method of claim 18 wherein said lowest concentration is 0%.

31. The method of claim 1 wherein at least two components are deposited and reacted with each other to form a new composition.

32. The method of claim 16 wherein said sample is a composite.

33. The method of claim 18 wherein said sample is a composite.

34. The method of claim 33 wherein said composite is a catalyst.

35. The method of claim 16 wherein each deposited component comprises a metal or metal oxide supported on a metal oxide support.

36. The method of claim 18 wherein each deposited component comprises a metal or metal oxide supported on a metal oxide support.

37. The method of claim 35 wherein said metal is a Group VIII metal.

38. The method of claim 36 wherein said metal is a Group VIII metal.

39. The method of claim 35 wherein said metal oxide support is alumina.

40. The method of claim 36 wherein said metal oxide support is alumina.

* * * * *